US00PP19802P2

(12) United States Plant Patent
Meinl

(10) Patent No.: US PP19,802 P2
(45) Date of Patent: Mar. 10, 2009

(54) **VARIETY OF *HYDRANGEA* PLANT NAMED 'HORSONN'**

(50) Latin Name: *Hydrangea macrophylla*
Varietal Denomination: Horsonn

(75) Inventor: Katrin Meinl, Dresden (DE)

(73) Assignee: Claus & Torsten Kühne GbR, Dresden (DE)

( * ) Notice: Subject to any disclaimer, the term of this patent is extended or adjusted under 35 U.S.C. 154(b) by 0 days.

(21) Appl. No.: 11/978,509

(22) Filed: Oct. 29, 2007

(51) Int. Cl.
*A01H 5/00* (2006.01)

(52) U.S. Cl. ..... Plt./250
(58) Field of Classification Search ..... Plt./250
See application file for complete search history.

*Primary Examiner*—Kent L Bell
(74) *Attorney, Agent, or Firm*—The Webb Law Firm

(57) ABSTRACT

A new and distinct *Hydrangea* plant having light pink flowers and a strong root system.

1 Drawing Sheet

Botanical classification: *Hydrangea macrophylla* hybrid.
Varietal denomination. 'HORSONN'.

BACKGROUND OF THE INVENTION

The present invention comprises a new and distinct cultivar of *Hydrangea* plant known by the varietal name 'Horsonn'. The new variety was discovered in 2001 in a breeding program in Dresden, Germany. The purpose of the breeding program was to develop *Hydrangeas* having light pink flowers. The new variety is the result of a cross between 'Königstein' (female parent, unpatented) and breeding selection no. 30-89/3 (male parent, unpatented). The inflorescence colour and foliage of the new variety are similar to its female parent, but 'Horsonn' exhibits a different vigour and inflorescence diameter. 'Horsonn' is a mophead like 'K önigstein', but their stem quality and root system differ. 'Horsonn' has a similar inflorescence diameter to its male parent, but differs in inflorescence colour and growth habit. The new variety was first asexually reproduced in 2001 via propagation by cuttings in Germany. The new variety has been trial and field tested in Germany and has been found to retain its distinctive characteristics and remain true to type through successive propagations.

The following traits distinguish 'Horsonn' as a new and distinct cultivar from other *Hydrangea* varieties known to the breeder:

1. Inflorescence size;
2. Stem quality;
3. Vigour;
4. Strong root system; and
5. Branching habit.

DESCRIPTION OF THE DRAWING

The accompanying photographic drawing illustrates the new variety, with the color being as nearly true as is possible with color illustrations of this type.

DESCRIPTION OF THE PLANT

Figure 1:
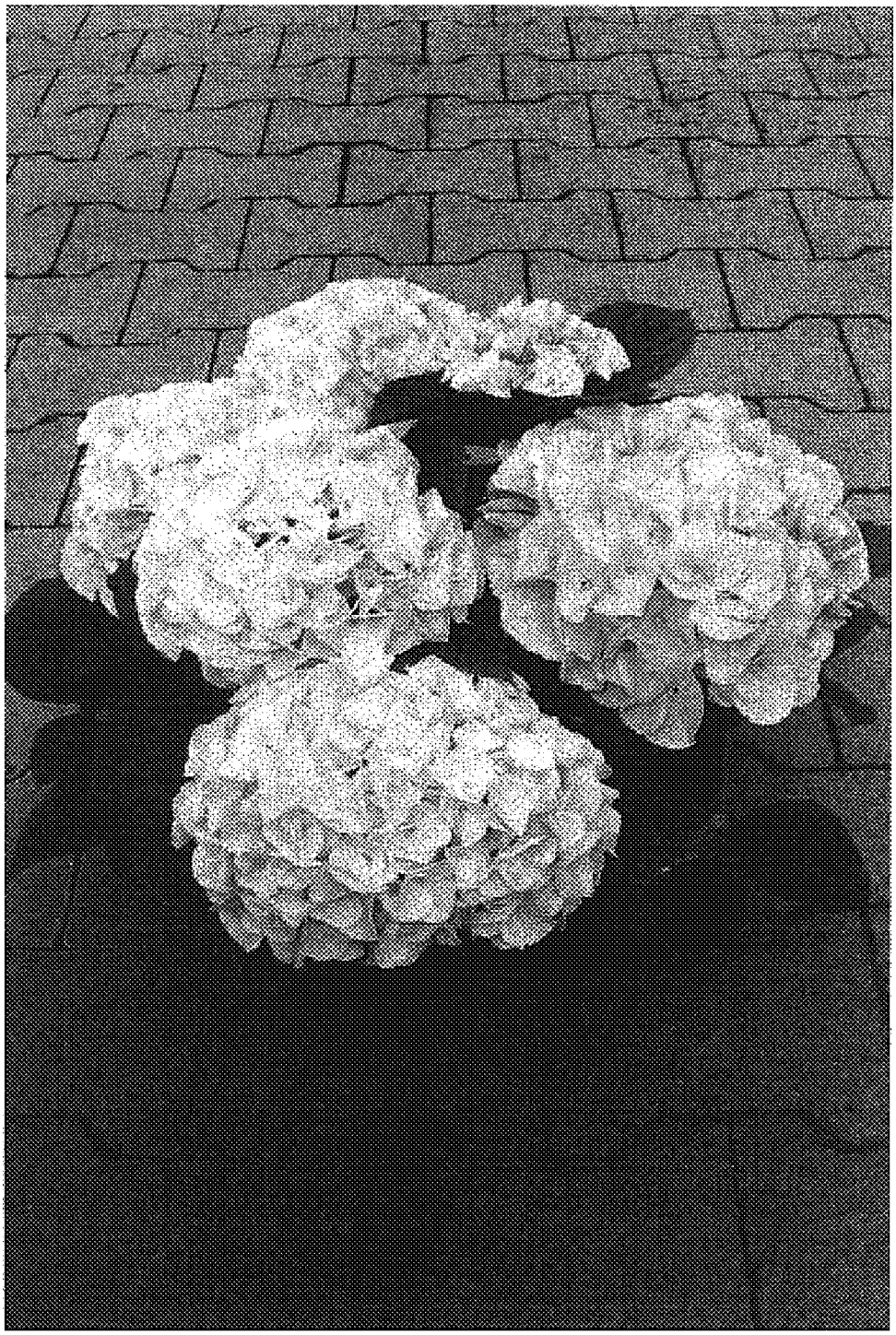
FIG. 1 is photograph of an entire plant of the new variety.

The following detailed description sets forth characteristics of the new cultivar. The plants were grown in 13 cm. pots in peat substrate at a pH of 6.0 and were 10 months past propagation when described. Measurements and color readings of the plants were taken in Dresden, Germany under natural light with a shadow present. Color references are primarily to the R.H.S. Colour Chart of the Royal Horticultural Society of London.

PLANT

Time to initiate roots: About 15 days at 18° C.
Time to develop roots: About 20 days at 18° C.
Rooting habit: Very strong and adventitious root system.
Time to produce a finished flowering plant from a rooted cutting: About 41 weeks in a 13 cm. container.
Form: Symmetrical.
Height (from media surface to top of foliage): 20.0 cm.
Height (from media surface to top of flowers): 30.0 cm.
Plant diameter: 45.0 cm.
Vigor: Strong.
Strength: No artificial support needed.
Branching habit: Well-branched.
Trunk:
- *Main trunk length.*—2.0 cm.
- *Diameter.*—1.2 cm.
- *Color.*—199A.
- *Texture.*—Woody.
- *Pubescence.*—Absent.
- *Internode length.*—2.0 cm.

Lateral branches:
- *Length.*—Young: 13.0 cm. Mature: 6.0 cm.
- *Diameter.*—Young: 0.7 cm. Mature: 0.9 cm.
- *Internode length.*—3.5 cm.
- *Texture.*—Smooth with dark lenticels.
- *Pubescence.*—Absent.
- *Color.*—Young: 143C. Mature: 199B.
- *Lenticel color.*—177A.

Foliage:
- *Arrangement.*—Opposite disposition.
- *Size of leaf.*—Length: 11.0 cm. Width: 8.0 cm.

*Shape of leaf* (*generally*).—Young: Ovate. Mature: Ovate.
*Shape of apex.*—Cuspidate.
*Shape of base.*—Obtuse.
*Texture.*—Matte.
*Aspect.*—Slightly undulate.
*Margin type.*—Serrate.
*Pubescence.*—None present.
*Color.*—Young leaves: Upper surface: 137A. Lower surface: 138A. Mature leaves: Upper surface: 139A. Lower surface: 138A.
*Petiole.*—Shape: U-shaped. Length: 2.5 cm. Diameter: 0.3 cm. Color: 138B.
*Veins.*—Venation type: Pinnate. Color: Upper surface: 138B. Lower surface: 138C.

FLOWER

Natural flowering season: July in Dresden, Germany.
Flower habit: Early blooming after 10 weeks of forcing.
Bud:
*Stage of development when described.*—At full colouration.
*Shape of cluster.*—Round.
*Diameter of cluster.*—8.0 cm.
*Number of buds per cluster.*—7 fertile, 19 sterile.
*Shape.*—Fertile: Round. Sterile: Round.
*Length.*—Fertile: 0.2 cm. Sterile: 0.1 cm.
*Width.*—Fertile: 0.3 cm. Sterile: 0.2 cm.
Inflorescence:
*Shape.*—Mophead.
*Length.*—10.0 cm.
*Diameter.*—17.0 cm.
*Average number of flowers per inflorescence.*—120.
*Average number of inflorescences per plant.*—8–10.
*Lastingness.*—Fertile: Three weeks. Sterile: Four weeks.
Petals:
*Number per flower.*—3 to 5.
*Color.*—Upper surface: 65D. Lower surface: 65D.
*Shape.*—Round.
*Length.*—0.2 cm.
*Width.*—0.1 cm.
*Apex.*—Pointy.
*Base.*—Obtuse.
*Margin.*—Entire.
*Texture.*—Smooth.
*Tonality from a distance.*—Mixed colour.
Sepals:
*Number per flower.*—4 to 5.
*Color.*—139D.
*Shape.*—Ovate.
*Length.*—0.1 cm.
*Width.*—0.1 cm.
*Apex.*—Pointy.
*Base.*—Obtuse.
*Margin.*—Entire.
*Texture.*—Smooth.
*Fused.*—Yes.
Petaloids:
*Quantity.*—3 to 5.
*Shape.*—Ovate.
*Color.*—Upper surface: 65A. Lower surface: 65B.
Pedicels: Fertile: 0.4 cm. Sterile: 2.6 cm.
*Diameter.*—Fertile: 0.1 cm. Sterile: 0.25 cm.
*Color.*—65C.
Peduncles:
*Length.*—4.5 cm.
*Diameter.*—0.3 cm.
*Texture.*—Smooth with dark lenticels.
*Color.*—137D, 178A lenticels.
Stamens:
*Number per fertile flower.*—7 to 9.
*Filament.*—Length: 0.2 cm. Color: 65D.
*Anthers.*—Shape: Round to elongated. Length: 0.1 cm. Color: 1D.
*Pollen.*—Color: 1D. Amount: Plentiful.
Pistils:
*Number.*—1 divided into 3 parts.
*Length.*—0.1 cm.
*Style.*—Length: 0.1 cm. Color: 65D.
*Stigma* (*divided into* 3 *parts*).—Color: 65D. Diameter: 0.15 cm.
*Ovaries* (*inferior*).—Length: 0.3 cm. Width: 0.2 cm. Color: 1D.
Fragrance: Fresh and "green".
Disease resistance: Tolerant to botrytis and powdery mildew.
Temperature tolerance: Medium, not fully winterhardy flower buds in Germany.
Drought tolerance: Medium.

I claim:

1. A new and distinct variety of *Hydrangea* plant substantially as shown and described herein.

* * * * *